(12) United States Patent
Mori

(10) Patent No.: US 7,620,078 B2
(45) Date of Patent: Nov. 17, 2009

(54) TUNABLE SEMICONDUCTOR LASER DEVICE, MANUFACTURING METHOD THEREFOR, AND GAS DETECTOR USING THEREWITH

(75) Inventor: Hiroshi Mori, Kawasaki (JP)

(73) Assignee: Anritsu Corporation, Atsugi-shi (JP)

( * ) Notice: Subject to any disclaimer, the term of this patent is extended or adjusted under 35 U.S.C. 154(b) by 476 days.

(21) Appl. No.: 11/578,637

(22) PCT Filed: Mar. 17, 2006

(86) PCT No.: PCT/JP2006/005360

§ 371 (c)(1),
(2), (4) Date: Oct. 17, 2006

(87) PCT Pub. No.: WO2006/098427

PCT Pub. Date: Sep. 21, 2006

(65) Prior Publication Data

US 2009/0086206 A1    Apr. 2, 2009

(30) Foreign Application Priority Data

Mar. 17, 2005    (JP) .............................. 2005-077373

(51) Int. Cl.
*H01S 3/10* (2006.01)
(52) U.S. Cl. .................... 372/20; 372/43.01; 372/87
(58) Field of Classification Search ............... 372/43.01, 372/20
See application file for complete search history.

(56) References Cited

FOREIGN PATENT DOCUMENTS

| JP | 3-196587 A | 8/1991 |
|---|---|---|
| JP | 04-072783 A | 3/1992 |
| JP | 06-310806 A | 11/1994 |
| JP | 9-36495 A | 2/1997 |
| JP | 09-074250 A | 3/1997 |
| JP | 2003-318483 A | 11/2003 |

(Continued)

OTHER PUBLICATIONS

Notification Concerning Transmittal of International Preliminary Report on Patentability and Written Opinion, Chapter I of the Patent Cooperation Treaty for PCT/JP2006/305360 mailed Sep. 27, 2007. 5 sheets.

*Primary Examiner*—Dung T Nguyen
(74) *Attorney, Agent, or Firm*—Frishauf, Holtz, Goodman & Chick, P.C.

(57) ABSTRACT

A tunable semiconductor laser device includes a wavelength control region that is formed to include an active layer formed above a semiconductor substrate in an optical waveguide which guides the light generated by the active layer and that includes in at least one portion a diffraction grating which selects light having a predetermined wavelength from the light generated by the active layer, a cladding layer, an insulation film formed above the cladding layer, a first driving electrode formed below the semiconductor substrate, a second driving electrode formed above the cladding layer, a heating portion that is formed above the insulation film and that is used to heat at least one portion of the wavelength control region, first and second heating terminals provided in the heating portion, and first and second connection lines that connect in series between the first and second driving electrodes through a power source. By tuning the current supplied from the power source to the first and second connection lines substantially connected in series through the heating portion, the tunable semiconductor laser device can be controlling the wavelength of the light derived to an outside from the optical waveguide.

28 Claims, 9 Drawing Sheets

FOREIGN PATENT DOCUMENTS

| | | |
|---|---|---|
| JP | 2004-031827 A | 1/2004 |
| JP | 2005-106521 A | 4/2005 |
| JP | 2006-261424 * | 9/2006 |

* cited by examiner

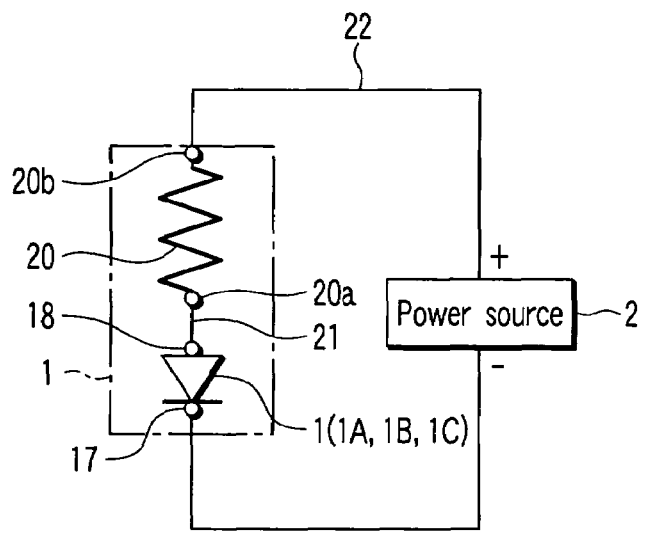
F I G. 2A
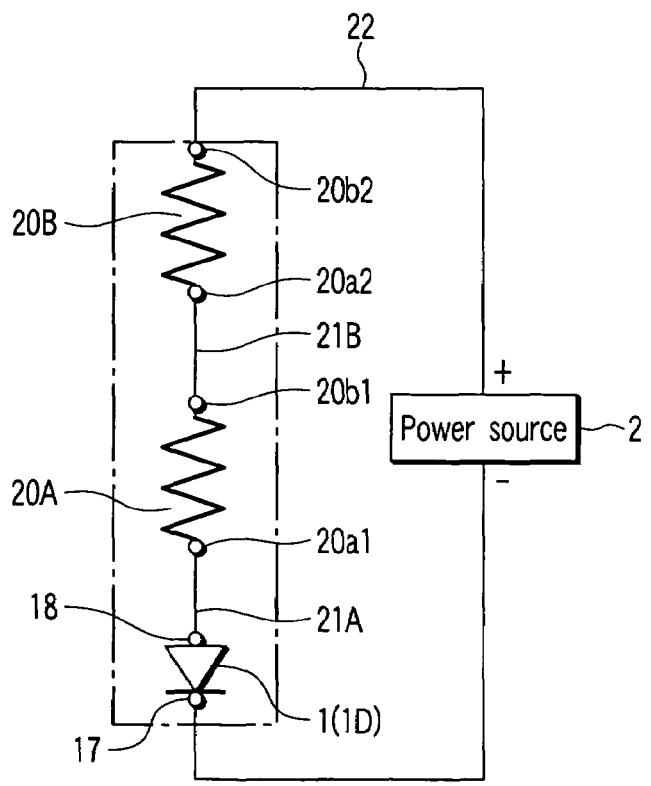
F I G. 2B

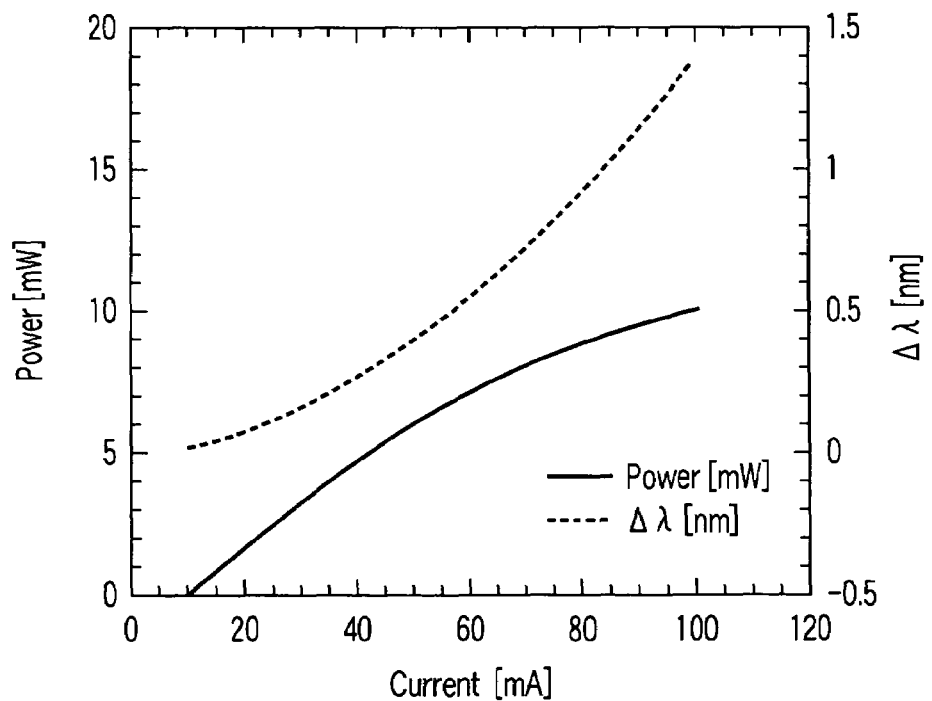
F I G. 7

TUNABLE SEMICONDUCTOR LASER DEVICE, MANUFACTURING METHOD THEREFOR, AND GAS DETECTOR USING THEREWITH

TECHNICAL FIELD

The present invention relates to a tunable semiconductor laser device, a manufacturing method therefor, and a gas detector using therewith. More particularly, the invention relates to a simply-configured tunable semiconductor laser device capable of outputting laser beam and controlling the wavelength, a manufacturing method therefor, and a gas detector using therewith.

BACKGROUND ART

Conventionally, there are known gas detectors of the type using a TDLAS (tunable diode laser absorption spectroscopy) scheme in which laser beam matched an absorption line wavelength of a detection target gas (such as a methane gas or alcoholic gas) is radiated into a detection space by using an absorption line peculiar to a gas. Then, the presence or absence, the concentration, and the like of the detection gas are detected by measuring the attenuated state of the radiated laser beam.

As semiconductor laser devices to be used with gas detectors of the above-described type, there are known tunable semiconductor lasers, such as a DFB (distributed feedback) laser disclosed in Patent Document 1 as described latter and a DBR (distributed Bragg reflector) laser disclosed in Patent Document 2 as described latter.

As shown in FIG. 9, the DFB laser, which is disclosed in Patent Document 1, is constructed such that, for example, an active layer 51 and an InP layer 52 are formed above a one-surface side of an n-InP substrate 53, and an n-type electrode 54 is formed on an opposite surface side of the n-InP substrate 53.

A $SiO_2$ insulation film 55 including a window and a p-type electrode 56 formed to contain Au for drive current injection are formed above the active layer 51.

Further, electrodes 59a and 59b for a resistive film 58 are formed respectively as islands in the right hand region of the p-type electrode 56.

Further, the resistive film 58 including a $SiO_2$ insulation film 57 and Pt is formed above the active layer 51.

In this case, two ends of the resistive film 58 are formed in contact with the electrodes 59a and 59b previously formed.

As shown in FIGS. 10A and 10B, the DBR laser, which is disclosed in Patent Document 2, includes a semiconductor optical device 64 and a heatsink 65, in which the semiconductor optical device 64 includes an optical waveguide 62 and a heating portion 63 formed via an insulation film 67 to heat at least one part of the optical waveguide 62; and the heatsink 65 is formed to mount the semiconductor optical device 64, to be in direct contact with the one part of the optical waveguide 62, and to be in contact with other parts of the optical waveguide 62 through a space portion 66.

In addition, a substrate 70 is periodically etched, and a corrugation-shaped diffraction grating 69 is thereby formed in a region 80 other than an active region 61 of the optical waveguide 62.

According to the DBR laser, among the regions other than the active region 61, a portion where the diffraction grating 69 is formed is referred to as a DBR region C, and the remaining portion is referred to as a phase control region B.

As shown in FIG. 10B, an InGaAsP guide layer to be used as a non-radiation region 80, and an InP cladding layer 71 are formed in the peripheral portion of the active region 61.

An n-type electrode 68 is formed on the upper surface of the active region 61 via the InP cladding layer 71 by performing vapor deposition of, for example, Au and Ge.

A p-type electrode (not shown) is formed on the bottom surface of the substrate 70 by performing vapor deposition of, for example, Au and Zn.

As DFB lasers having a configuration different from that of the DFB laser disclosed in Patent Document 1 as described above are, for example, a partial diffraction grating semiconductor laser (PC-LD) disclosed in Patent Document 3 as described latter; and a distributed feedback semiconductor laser having two diffraction gratings, which laser is disclosed in Patent Document 4 as described latter.

Patent Document 1: Jpn. Pat. Appln. KOKAI Publication No. 4-72783

Patent Document 2: Jpn. Pat. Appln. KOKAI Publication No. 9-74250

Patent Document 3: Jpn. Pat. Appln. KOKAI Publication No. 6-310806

Patent Document 4: Jpn. Pat. Appln. KOKAI Publication No. 2004-31827

DISCLOSURE OF INVENTION

In the case where the tunable semiconductor laser described above is used as the light source of the gas detector to thereby detect the detection target gas in the detection space by using the TDLAS scheme, operation is performed as follows. The semiconductor laser is modulated, the wavelength of the radiation beam is locked thereby to the absorption line peculiar to the detection target gas, the wavelength-locked laser beam is radiated towards the detection space, and reflected light from the detection space in association with the radiation of the laser beam is received.

In this case, the semiconductor laser has characteristics in that the wavelength of the radiation beam is determined depending on the refractive index of the optical waveguide, and the refractive index of the optical waveguide is determined depending on the temperature or the carrier density (injection current).

Other characteristics are that, in the event that the temperature is varied, while the response speed when the laser beam has been modulated to be locked to the absorption line peculiar to the detection target gas is low, the variation range of the refractive index is increased, so that a large tunable wavelength range can be set.

On the other hand, there are characteristics in that, in the event that the carrier density is varied, while the response speed when the laser beam has been modulated to be locked to the absorption line peculiar to the detection target gas is high, the refractive index is saturated at a certain level of the carrier density, such that the variation range is narrow, and hence the tunable wavelength range cannot be set to be so large.

In the case where the semiconductor laser having above-described characteristics is modulated to lock the wavelength of the radiation beam to the absorption line peculiar to the detection target gas, the absorption line wavelength of the detection target gas and the range including the center of the absorption line wavelength is different. Thus, the wavelength of the laser beam has to be made tunable to enable a sufficient wavelength tunable wavelength range corresponding to the kind of detection target gas.

However, it is known that, in the gas detection according to TDLAS schemes of the above-described type, any kind of detection target gas is sufficiently addressable as long as the gas has a modulation frequency of about 10 KHz. Thus, even when precedence is placed on the magnitude of refraction index variation over the response speed, the gas can be sufficiently traced only by changing the temperature.

Patent Document 5 as described latter, discloses a portable gas concentration measuring device miniaturized so as to be handy and capable of easily detecting, for example, the concentration and the presence or absence of gas. However, in the case of such a portable gas concentration measuring device, the component mounting space in a housing is limited, power consumption has to be restrained since the device is driven with battery, and no more than a single power source can be provided in the housing.

Patent Document 5: Jpn. Pat. Appln. KOKAI Publication No. 2005-106521

Therefore, as a semiconductor laser for use with such a portable gas concentration measuring device of the above-described type, a semiconductor laser device is demanded that is capable of outputting laser and tuning the wavelength by using a single power source and, concurrently, that enables a sufficient tunable wavelength range to be obtained.

However, in the semiconductor laser devices disclosed in, Patent Document 1 and Patent Document 2 as described above, while the laser output and the wavelength can be controlled independently of each other, a heating power source and a laser driving power source are separately configured. In this case, problems arise in that not only the configuration is complex, but also the configuration cannot be adapted to, for example, the portable gas concentration measuring device in which no more than a single power source can be provided in the housing.

In order to solve the problems with the conventional techniques as described above, an object of the present invention is to provide a tunable semiconductor laser device, a manufacturing method therefor, and a gas detector using therewith, in which, with a simple configuration, in the event of gas detection by a TDLAS scheme, the semiconductor laser device is capable of controlling the wavelength and the laser output by current of single channel in a sufficient tunable wavelength range, and is therefore capable of implementing sharing of a single power source for a heating power source and laser driving power source. Consequently, the mounting space required in practical mounting is reduced.

In order to achieve the above object, according to a first aspect of the present invention, there is provided a tunable semiconductor laser device, comprising: a semiconductor substrate (10); an active layer (12) that is formed above the semiconductor substrate and that generates light; a wavelength control region (D) that is formed to include the active layer, that is formed in an optical waveguide which guides the light generated by the active layer, and that includes in at least one portion a diffraction grating (14) which selects light having a predetermined wavelength from the light generated by the active layer; a cladding layer (13) formed above the optical waveguide; an insulation film (19) formed above the cladding layer; a first driving electrode (17) formed below the semiconductor substrate; a second driving electrode (18) formed above the cladding layer; a heating portion (20) that is formed above the insulation film and that is used to heat at least one portion of the wavelength control region; a first heating terminal (20a) and a second heating terminal (20b) that are provided in the heating portion (20); a first connection line (21) that connects between the second driving electrode and the first heating terminal; and a second connection line (22) that connects between the first driving electrode and the second heating terminal through a power source, wherein current supplied from the power source to the first and second connection lines connected in series through the heating portion is tuned, whereby the wavelength of the light derived to an outside from the optical waveguide can be controlled.

In addition, according to a second aspect of the present invention, there is provided the tunable semiconductor laser device according to the first aspect, wherein: the wavelength control region includes a distributed Bragg reflector region (C) formed of the diffraction grating and a phase adjust region (B) adjacent to the distributed Bragg reflector region; and the heating portion is configured to be capable of heating at least one portion of the phase adjust region.

In addition, according to a third aspect of the present invention, there is provided the tunable semiconductor laser device according to the second aspect, wherein the heating portion is configured further to be capable of uniformly heating an overall area of the distributed Bragg reflector region.

In addition, according to a fourth aspect of the present invention, there is provided the tunable semiconductor laser device according to the first aspect, wherein: the wavelength control region is formed of one diffraction grating; and the heating portion is configured to be capable of uniformly heating an overall area of the one diffraction grating.

In addition, according to a fifth aspect of the present invention, there is provided the tunable semiconductor laser device according to the fourth aspect, wherein the one diffraction grating is formed across an overall area of the optical waveguide.

In addition, according to a sixth aspect of the present invention, there is provided the tunable semiconductor laser device according to the fourth aspect, wherein the one diffraction grating is formed in one portion of the optical waveguide.

In addition, according to a seventh aspect of the present invention, there is provided the tunable semiconductor laser device according to the first aspect, wherein: the wavelength control region is formed of a plurality of diffraction gratings (14a, 14b) formed in a plurality of portions of the optical waveguide; and the heating portion is configured to be capable of heating the plurality of diffraction gratings so that respective wavelengths selected by respective ones of the plurality of diffraction gratings are identical to one another.

In addition, according to an eighth aspect of the present invention, there is provided the tunable semiconductor laser device according to the seventh aspect, wherein the heating portion is formed of a plurality of heating portions (20A, 20B) that discretely heat the plurality of diffraction gratings, and the plurality of heating portions are connected in series.

In addition, according to a ninth aspect of the present invention, there is provided the tunable semiconductor laser device according to the first aspect, wherein the heating portion is formed of a thin-film resistor.

In addition, according to a tenth aspect of the present invention, there is provided the tunable semiconductor laser device according to the first is aspect, being employed in a gas detector that radiates laser beam having a predetermined wavelength into a detection space, and that performs gas detection by using a tunable diode laser absorption spectroscopy scheme utilizing a characteristic that the laser beam is attenuated by a detection target gas.

In addition, in order to achieve the above object, according to an eleventh aspect of the present invention, there is provided a gas detector that includes a tunable semiconductor laser device, that radiates laser beam having a predetermined wavelength into a detection space, and that performs gas detection by using a tunable diode laser absorption spectroscopy scheme utilizing a characteristic that the laser beam is attenuated by a detection target gas, wherein the tunable semiconductor laser device comprises: a semiconductor substrate (10); an active layer (12) that is formed above the semiconductor substrate and that generates light; a wavelength control region (D) that is formed to include the active layer, that is formed in an optical waveguide which guides the light generated by the active layer, and that includes in at least one portion a diffraction grating (14) which selects light having a predetermined wavelength from the light generated by the active layer; a cladding layer (13) formed above the optical waveguide; an insulation film (19) formed above the cladding layer; a first driving electrode (17) formed below the semiconductor substrate; a second driving electrode (18) formed above the cladding layer; a heating portion (20) that is formed above the insulation film and that is used to heat at least one portion of the wavelength control region; a first heating terminal (20a) and a second heating terminal (20b) that are provided in the heating portion (20); a first connection line (21) that connects between the second driving electrode and the first heating terminal; and a second connection line (22) that connects between the first driving electrode and the second heating terminal through a power source, wherein current supplied from the power source to the first and second connection lines connected in series through the heating portion is tuned, whereby the wavelength of the light derived to an outside from the optical waveguide can be controlled.

In addition, according to a twelfth aspect of the present invention, there is provided the gas detector according to the eleventh aspect, wherein: the wavelength control region includes a distributed Bragg reflector region (C) formed of the diffraction grating and a phase adjust region (B) adjacent to the distributed Bragg reflector region; and the heating portion is configured to be capable of heating at least one portion of the phase adjust region.

In addition, according to a thirteenth aspect of the present invention, there is provided the gas detector according to the twelfth aspect, wherein the heating portion is configured further to be capable of uniformly heating an overall area of the distributed Bragg reflector region.

In addition, according to a fourteenth aspect of the present invention, there is provided the gas detector according to the eleventh aspect, wherein: the wavelength control region is formed of one diffraction grating; and the heating portion is configured to be capable of uniformly heating an overall area of the one diffraction grating.

In addition, according to a fifteenth aspect of the present invention, there is provided the gas detector according to the fourteenth aspect, wherein the one diffraction grating is formed across an overall area of the optical waveguide.

In addition, according to a sixteenth aspect of the present invention, there is provided the gas detector according to the fourteenth aspect, wherein the one diffraction grating is formed in one portion of the optical waveguide.

In addition, according to a seventeenth aspect of the present invention, there is provided the gas detector according to the eleventh aspect, wherein: the wavelength control region is formed of a plurality of diffraction gratings (14a, 14b) formed in a plurality of portions of the optical waveguide; and the heating portion is configured to be capable of heating the plurality of diffraction gratings so that respective wavelengths selected by respective ones of the plurality of diffraction gratings are identical to one another.

In addition, according to a eighteenth aspect of the present invention, there is provided the gas detector according to the seventeenth aspect, wherein the heating portion is formed of a plurality of heating portions (20A, 20B) that discretely heat the plurality of diffraction gratings, and the plurality of heating portions are connected in series.

In addition, according to a nineteenth aspect of the present invention, there is provided the gas detector according to the eleventh aspect, wherein the heating portion is formed of a thin-film resistor.

In addition, in order to achieve the above object, according to a twentieth aspect of the present invention, there is provided a method for manufacturing a tunable semiconductor laser device, the method comprising: a step of forming an optical waveguide above a semiconductor substrate, the optical waveguide including an active layer (12) that generates light, and a wavelength control region (D) including in at least one portion a diffraction grating (14) which selects and reflects light having a predetermined wavelength from the light generated by the active layer; a step of forming a cladding layer (13) above the optical waveguide; a step of forming an insulation film (19) above the cladding layer; a step of forming a first driving electrode (17) below the semiconductor substrate; a step of forming a second driving electrode (18) above the cladding layer; a step of forming a heating portion (20) above the insulation film, for being used to heat at least one portion of the wavelength control region; a step of forming a first heating terminal (20a) and a second heating terminal (20b) in the heating portion (20); a step of connecting between the second driving electrode and the first heating terminal by using a first connection line (21); and a step of connecting between the first driving electrode and the second heating terminal through a power source by using a second connection line (22), wherein current supplied from the power source to the first and second connection lines connected in series through the heating portion is tuned, whereby the wavelength of the light derived to an outside from the optical waveguide can be controlled.

In addition, according to a twenty-first aspect of the present invention, there is provided the method for manufacturing a tunable semiconductor laser device according to the twentieth aspect, wherein: the wavelength control region includes a distributed Bragg reflector region (C) formed of the diffraction grating and a phase adjust region (B) adjacent to the distributed Bragg reflector region; and the heating portion is configured to be capable of heating at least one portion of the phase adjust region.

In addition, according to a twenty-second aspect of the present invention, there is provided the method for manufacturing a tunable semiconductor laser device according to the twenty-first, wherein the heating portion is configured further to be capable of uniformly heating an overall area of the distributed Bragg reflector region.

In addition, according to a twenty-third aspect of the present invention, there is provided the method for manufacturing a tunable semiconductor laser device according to the twentieth aspect, wherein: the wavelength control region is formed of one diffraction grating; and the heating portion is configured to be capable of uniformly heating the overall area of the one diffraction grating.

In addition, according to a twenty-fourth aspect of the present invention, there is provided the method for manufacturing a tunable semiconductor laser device according to the twenty-third aspect, wherein the one diffraction grating is formed across an overall area of the optical waveguide.

In addition, according to a twenty-fifth aspect of the present invention, there is provided the method for manufacturing a tunable semiconductor laser device according to the twenty-third aspect, wherein the one diffraction grating is formed in one portion of the optical waveguide.

In addition, according to a twenty-sixth aspect of the present invention, there is provided the method for manufacturing a tunable semiconductor laser device according to the twentieth aspect, wherein: the wavelength control region is formed of a plurality of diffraction gratings (14a, 14b) formed in a plurality of portions of the optical waveguide; and the heating portion is configured to be capable of heating the plurality of diffraction gratings so that respective wavelengths selected by respective ones of the plurality of diffraction gratings are identical to one another.

In addition, according to a twenty-seventh aspect of the present invention, there is provided the method for manufacturing a tunable semiconductor laser device according to the twenty-sixth aspect, wherein the heating portion is formed of a plurality of heating portions (20A, 20B) that discretely heat the plurality of diffraction gratings, and the plurality of heating portions are connected in series.

In addition, according to a twenty-eighth aspect of the present invention, there is provided the method for manufacturing a tunable semiconductor laser device according to the twentieth aspect, wherein the heating portion is formed of a thin-film resistor.

According to the present invention, at least one part of the phase adjust region can be heated by the heating portion. Thereby, the tunable semiconductor laser device can be realized in which the refraction index of the optical waveguide of the part is largely varied, whereby the wavelength and the laser output can be controlled in a desired tunable wavelength range by using the current of the single channel.

In addition, according to the present invention, the tunable semiconductor laser device can be realized in which the wavelength and the laser output can be controlled by sharedly using the single power source in the event of gas detection by the TDLAS scheme, and hence the configuration is simplified. Accordingly, even in a portable gas detector in which no more than one power source can be provided in a housing, the mounting space required in practical mounting can be as small as possible.

Further, according to the present invention, the heating portion is arranged to not directly heat the active layer, whereby the tunable semiconductor laser device enabling an enhanced lifetime of the semiconductor laser device can be realized.

BRIEF DESCRIPTION OF DRAWINGS

FIG. 2A is an equivalent circuit diagram showing one example of an electrical configuration of an essential portion of the tunable semiconductor laser device in accordance with the present invention.

FIG. 2B is an equivalent circuit diagram showing another example of an electrical configuration of an essential portion of the tunable semiconductor laser device in accordance with the present invention.

FIG. 7 is a diagram showing output characteristics of the tunable semiconductor laser device in accordance with the present invention.

BEST MODE FOR CARRYING OUT THE INVENTION

Embodiments of the present invention will be described below with reference to the drawings.

First Embodiment

To begin with, a first embodiment of a tunable semiconductor laser device in accordance with the present invention will be described herebelow with reference to FIG. 1A.

Figure 1A:
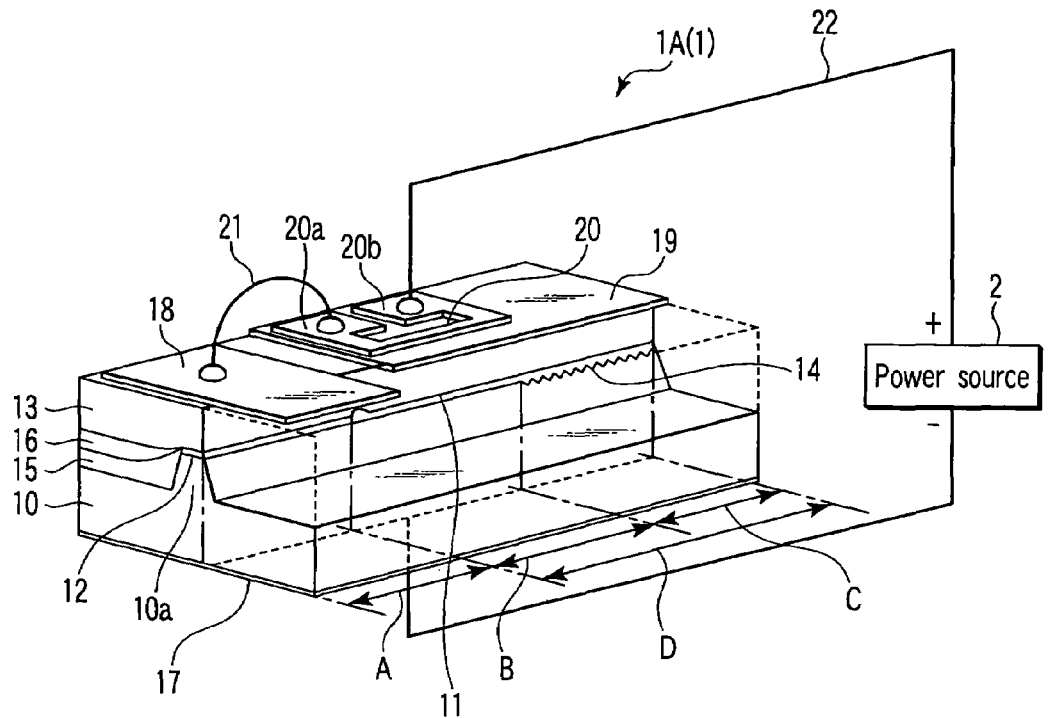
FIG. 1A is a schematic perspective view showing the configuration of a first embodiment of a tunable semiconductor laser device in accordance with the present invention.

FIG. 1A is a schematic perspective view showing the configuration of the first embodiment of the tunable semiconductor laser device in accordance with the present invention.

With reference to FIG. 1A, in the tunable semiconductor laser device, which is represented by numeral 1A(1), of the first embodiment, an optical waveguide is configured of three regions, namely, an active region A, a phase adjust region B, and a DBR region C.

As shown in FIG. 1A, a mesa 10a in a cross-sectionally trapezoidal shape is formed to extend along the length direction (light radiation direction) in an upper central portion of an n-InP substrate 10 provided as a semiconductor substrate for the use of making a multilayered semiconductor layer.

An active layer 12 for generating the light, and a p-InP cladding layer 13 are sequentially formed above the mesa 10a.

A p-InP buried layer 15 and an n-InP buried layer 16 are formed on two sides of the mesa 10a, whereby a narrowed portion of a current path supplied between a pair of electrodes described further below is secured, and a stripe optical waveguide is formed.

A pair of electrodes 17 and 18 are formed on the obverse and reverse surfaces of the semiconductor layer made as described above. More particularly, an n-type electrode 17 (first driving electrode) and p-type electrode 18 (second driving electrode) each made of metal film such as Au are respectively formed.

Although not shown, a contact layer for facilitating the injection of current may be formed between the p-InP cladding layer 13 and the p-type electrode 18.

Preferably, the material used for the contact layer is p-InGaAs or p-InGaAsP, for example.

In the example shown in FIG. 1A, the n-type electrode 17 is formed on the reverse face of the n-InP substrate 10, and the p-type electrode 18 is formed on a portion (front portion on the lefthand side) of the surface of the p-InP cladding layer 13.

In the semiconductor laser device 1A, an optical waveguide for distributing the light is formed that is constituted of an active region A where an active layer 12 for generating the light is formed, a first passive region ("phase adjust region B", hereafter) provided continuously to the active region A, and a second passive region ("Bragg reflector region (or DBR region C)", hereafter) provided continuously to the phase adjust region B and having a one-end side (righthand portion) where a diffraction grating 14 is formed.

Reference numeral 11 denotes a light guide layer forming a part of the optical waveguide.

A heating portion 20 formed from a thin film resistor made of Pt, Au, or the like is formed on the phase adjust region B of the surface of the p-InP cladding layer 13 via an insulation layer 19.

A first heating terminal 20a and a second heating terminal 20b are formed in the heating portion 20.

The heating portion 20 is connected via wire to a single external power source 2 in series with the pair of electrodes 17 and 18.

In this case, the second driving electrode 18 (p-type electrode) and the first heating terminal 20a are interconnected through a first connection line 21 formed of a bonding wire or the like. The first driving electrode 17 (n-type electrode) and the second heating terminal 20b are interconnected via the external power source 2 through a second connection line 22 formed of a bonding wire or the like.

In this manner, as shown in FIG. 2A, an equivalent circuit is configured such that the pair of electrodes 17 and 18 and the heating portion 20 are connected in series to the single external power source 2 in the tunable semiconductor laser device 1.

The current of the single channel is supplied as driving power in synchronism from the single external power source 2 to both the interconnected portions between the pair of electrodes 17 and 18 and the heating portion 20.

More particularly, as shown in FIG. 1A, in the tunable semiconductor laser device 1 of the first embodiment, a wavelength control region D is constituted of the distributed Bragg reflector (DBR) region C, which is formed of the diffraction grating 14 provided in one part of the wavelength control region D, and the phase adjust region B located adjacent to the DBR region C.

The heating portion 20 is formed to be capable of heating at least one part of the phase adjust region B in the event of heating the phase adjust region B included in the wavelength control region D.

Thus, according to the first embodiment, the tunable semiconductor laser device 1 is realized in which at least one part of the phase adjust region B is heated by the heating portion 20 to largely vary the refractive index of the optical waveguide in that part, whereby the wavelength of the light generated by the active layer 12 and laser output can be controlled in a desired tunable wavelength range by using the single-channel current.

In addition, according to the first embodiment, the tunable semiconductor laser device 1 is realized in which the wavelength of the light generated by the active layer 12 and the laser output can be controlled by sharedly using the single external power source 2. Further, since the configuration is simplified, even in the case of adaptation to a portable gas detector in which no more than a single power source can be provided in a housing, the mounting space required in practical mounting can be as small as possible.

Further, according to the first embodiment, the heating portion 20 is formed only on the phase adjust region B, and the active region A for generating the light is not directly heated by the heating portion 20, whereby the tunable semiconductor laser device 1 enabling enhanced lifetime is realized.

In the first embodiment, while description has been made with reference to the example in which the heating portion 20 is formed only on the phase adjust region B, the configuration is not limited thereto.

Figure 1B:
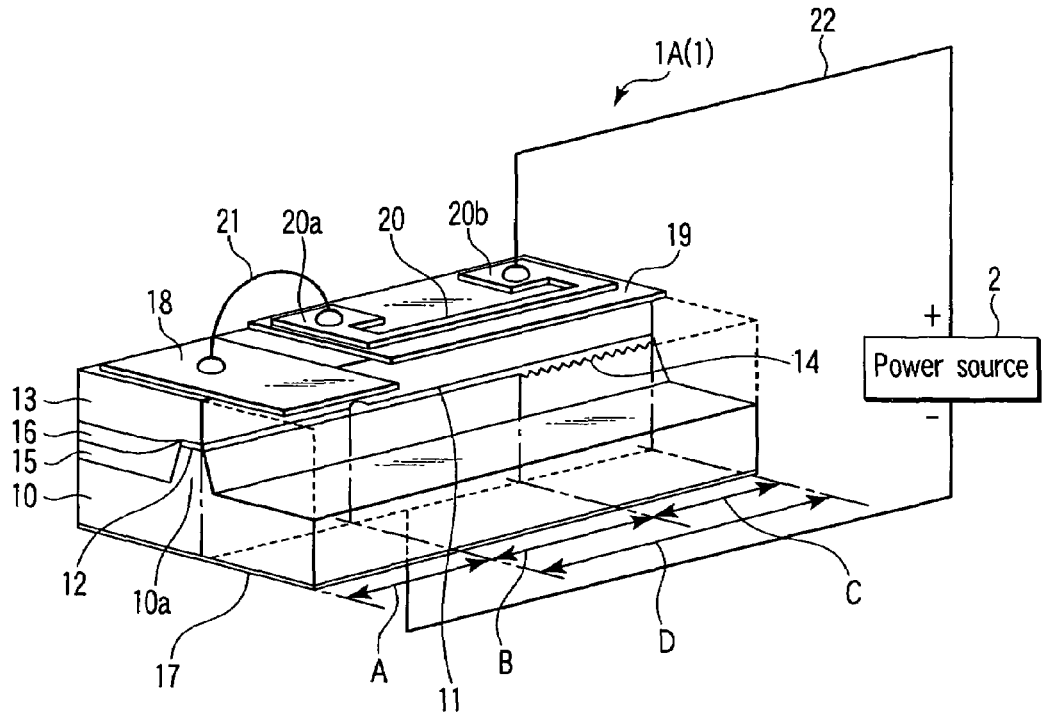
FIG. 1B is a schematic perspective view showing the configuration of a modified example of the first embodiment of the tunable semiconductor laser device in accordance with the present invention.

For example, as shown in FIG. 1B, the configuration may be such that the heating portion 20 uniformly heats the entirety of the DBR region C in addition to the entirety or one part of the phase adjust region B.

Modified Example of First Embodiment

A modified example of the first embodiment of the tunable semiconductor laser device in accordance with the present invention will be described herebelow with reference to FIG. 1B.

FIG. 1B is a schematic perspective view showing the configuration of the modified example of the first embodiment of the tunable semiconductor laser device in accordance with the present invention.

In FIG. 1B, like reference numerals designate portions similar in configuration to those of the tunable semiconductor laser device of the first embodiment shown in FIG. 1A, and descriptions thereof will be omitted herefrom.

With reference to FIG. 1B, the tunable semiconductor laser device 1A(1) according to the modified example of the first embodiment is similar to the first embodiment. The wavelength control region D is constituted of the distributed Bragg reflector (DBR) region C formed of the diffraction grating 14 provided in one part of the wavelength control region D, and the phase adjust region B located adjacent to the DBR region C.

The heating portion 20 is formed to be capable of heating at least one part of the phase adjust region B and uniformly heating the entire DBR region C in the event of heating the phase adjust region B and the DBR region C that are included in the wavelength control region D.

Thus, according to the modified example of the first embodiment, the tunable semiconductor laser device 1 is realized in which at least one part of the phase adjust region B is heated by the heating portion 20 and the entirety of the DBR region C is uniformly heated to cause the refractive index of the optical waveguide in the portion to vary even larger than in the case of the first embodiment, whereby the wavelength of the light generated by the active layer 12 and laser output can be controlled in a desired tunable wavelength range by using the single-channel current.

Second Embodiment

A second embodiment of a tunable semiconductor laser device in accordance with the present invention will be described in detail below with reference to FIG. 3.

Figure 3:
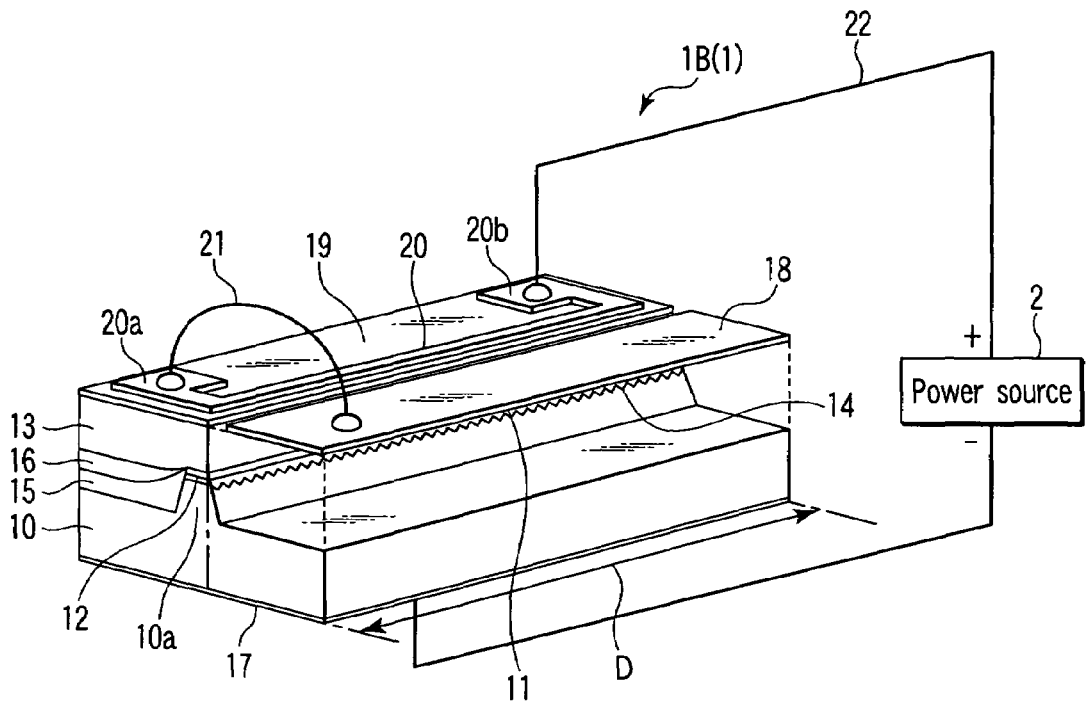
FIG. 3 is a schematic perspective view showing the configuration of a second embodiment of a tunable semiconductor laser device in accordance with the present invention.

FIG. 3 is a schematic perspective view showing the configuration of the second embodiment of the tunable semiconductor laser device in accordance with the present invention.

With reference to FIG. 3, the tunable semiconductor laser device, which is represented by numeral 1B(1), of the second embodiment is a DFB laser that includes a diffraction grating 14 formed on the entirety of a light guide layer 11 underlying an active layer 12.

As shown in FIG. 3, a mesa 10a in a cross-sectionally trapezoidal shape is formed to extend along the length direction (light radiation direction) in an upper central portion of an n-InP substrate 10 provided as a semiconductor substrate for the use of making a multilayered semiconductor layer.

The light guide layer 11 on the entirety of which the diffraction grating 14 is formed, the active layer 12 for generating light, and a p-InP cladding layer 13 are sequentially formed above the mesa 10a.

A p-InP buried layer 15 and an n-InP buried layer 16 are formed on two sides of the mesa 10a, whereby a narrowed portion of a current path supplied between a pair of electrodes described further below is secured, and a stripe optical waveguide is formed.

A pair of electrodes 17 and 18 are formed on the obverse and reverse surfaces of the semiconductor layer made as described above. More particularly, an n-type electrode 17 (first driving electrode) and a p-type electrode 18 (second driving electrode) each made of metal film such as Au are respectively formed.

In the example shown in FIG. 3, the n-type electrode 17 is formed on the reverse face of the n-InP substrate 10, and the p-type electrode 18 is formed on a portion (substantially half portion on the righthand side, excluding the upper surface of the active layer 12) of the surface of the p-InP cladding layer 13.

A heating portion 20 formed from a thin film resistor made of Pt, Au, or the like is formed via an insulation layer 19 on the upper surface of the p-InP cladding layer 13. The heating portion is formed there in such a manner as to cover the overall area of the diffraction grating 14 formed as the wavelength control region D on the overall area of the light guide layer 11.

A first heating terminal 20a and a second heating terminal 20b are formed in the heating portion 20.

The heating portion 20 is connected via wire to a single external power source 2 in series with the pair of electrodes 17 and 18.

In this case, the second driving electrode 18 (p-type electrode) and the first heating terminal 20a are interconnected through a first connection line 21 formed of a bonding wire or the like. The first driving electrode 17 (n-type electrode) and the second heating terminal 20b are interconnected via the external power source 2 through a second connection line 22 formed of a bonding wire or the like.

In this manner, as shown in FIG. 2A, an equivalent circuit is configured such that the pair of electrodes 17 and 18 and the heating portion 20 are connected in series to the single external power source 2 in the tunable semiconductor laser device 1.

The current of the single channel is supplied as driving power in synchronism from the single external power source 2 to both the interconnected portions between the pair of electrodes 17 and 18 and the heating portion 20.

Thus, according to the second embodiment, the tunable semiconductor laser device 1 is realized in which the overall area of the diffraction grating 14 formed in the overall area of the light guide layer 11 is heated by the heating portion 20 to largely vary the refractive index of the optical waveguide in that part, whereby the wavelength of the light generated by the active layer 12 and the laser output can be controlled in a desired tunable wavelength range by using the single-channel current.

In addition, according to the second embodiment, the tunable semiconductor laser device 1 is realized in which the wavelength of the light generated in the active region A and the laser output can be controlled by sharedly using the single external power source 2. Further, in this case, since the configuration is simplified, even in the case of adaptation to a portable gas detector in which no more than a single power source can be provided in a housing, the mounting space in the event of practical mounting can be as small as possible.

Third Embodiment

A third embodiment of a tunable semiconductor laser device in accordance with the present invention will be described in detail below with reference to FIG. 4.

Figure 4:
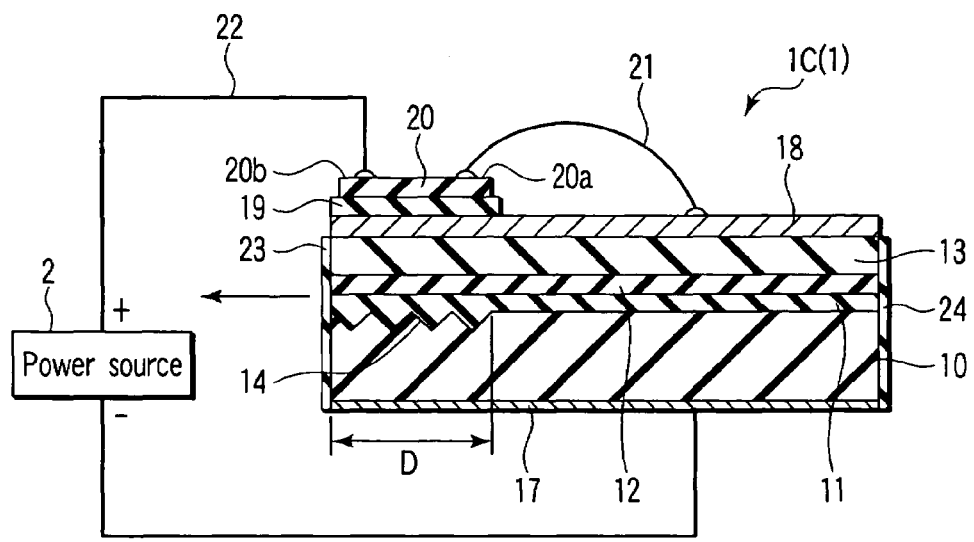
FIG. 4 is a schematic perspective view showing the configuration of a third embodiment of a tunable semiconductor laser device in accordance with the present invention.

FIG. 4 is a cross sectional view showing the configuration of the third embodiment of the tunable semiconductor laser device in accordance with the present invention.

With reference to FIG. 4, the tunable semiconductor laser device, which is represented by numeral 1C(1), of the third embodiment is a partial diffraction grating semiconductor laser (PC-LD) in which a diffraction grating 14 of the type formed in the tunable semiconductor laser device 1B(1) of the second embodiment is not formed in the overall area on the active layer 12 but is partially formed on an end face side in the radiation direction A light guide layer 11, the active layer 12 for generating light, and a p-InP cladding layer 13 are sequentially formed above the diffraction grating 14.

Thereafter, similarly as in the second embodiment, a p-InP buried layer and n-InP buried layer (not shown) are formed in a regular burying and growing process.

Then, an antireflective film 23 (AR coating) is formed on the laser radiation surface and a high reflective film 24 (HR coating) is formed on the reflective surface.

A pair of electrodes 17 and 18 are formed on the obverse and reverse surfaces of the semiconductor crystal made as described above. More particularly, an n-type electrode 17 (first driving electrode) and p-type electrode 18 (second driving electrode) each made of a metal electrode are respectively formed.

In the example shown in FIG. 4, the n-type electrode 17 is formed on the reverse face of the n-InP substrate 10, and the p-type electrode 18 is formed on a portion (portion on the lefthand side) of the surface of the p-InP cladding layer 13.

A heating portion 20 formed from a thin film resistor made of Pt, Au, or the like is formed via an insulation layer 19 on the upper surface of the p-InP cladding layer 13. The heating portion is formed there in such a manner as to cover the overall area of the diffraction grating 14 partially formed on the side of the radiation surface.

A first heating terminal 20a and a second heating terminal 20b are formed in the heating portion 20.

The heating portion 20 is connected via wire to a single external power source 2 in series with the pair of electrodes 17 and 18.

In this case, the second driving electrode 18 (p-type electrode) and the first heating terminal 20a are interconnected through a first connection line 21 formed of a bonding wire or the like. The first driving electrode 17 (n-type electrode) and the second heating terminal 20b are interconnected via the external power source 2 through a second connection line 22 formed of a bonding wire or the like.

In this manner, as shown in FIG. 2A, an equivalent circuit is configured such that the pair of electrodes 17 and 18 and the heating portion 20 are connected in series to the single external power source 2 in the tunable semiconductor laser device 1.

Current of a single channel is supplied as driving power in synchronism from the single external power source 2 to both the interconnected portions between the pair of electrodes 17 and 18 and the heating portion 20.

Thus, according to the third embodiment, the tunable semiconductor laser device 1 is realized in which the overall area of the diffraction grating 14 partially formed on the side of the radiation surface of the light guide layer 11 is heated by the heating portion 20 to largely vary the refractive index of the light guide layer 11 in that area, whereby the light wavelength generated by the active layer 12 and the laser output can be controlled in a desired tunable wavelength range by using the single-channel current.

In addition, according to the third embodiment, the wavelength of the light generated by the active layer 12 and laser output can be controlled by sharedly using the single external power source 2. Further, since the configuration is simplified, even in the case of adaptation to a portable gas detector in which no more than a single power source can be provided in a housing, the mounting space in the event of practical mounting can be as small as possible.

Fourth Embodiment

A fourth embodiment of a tunable semiconductor laser device in accordance with the present invention will be described in detail below with reference to FIG. 5.

Figure 5:
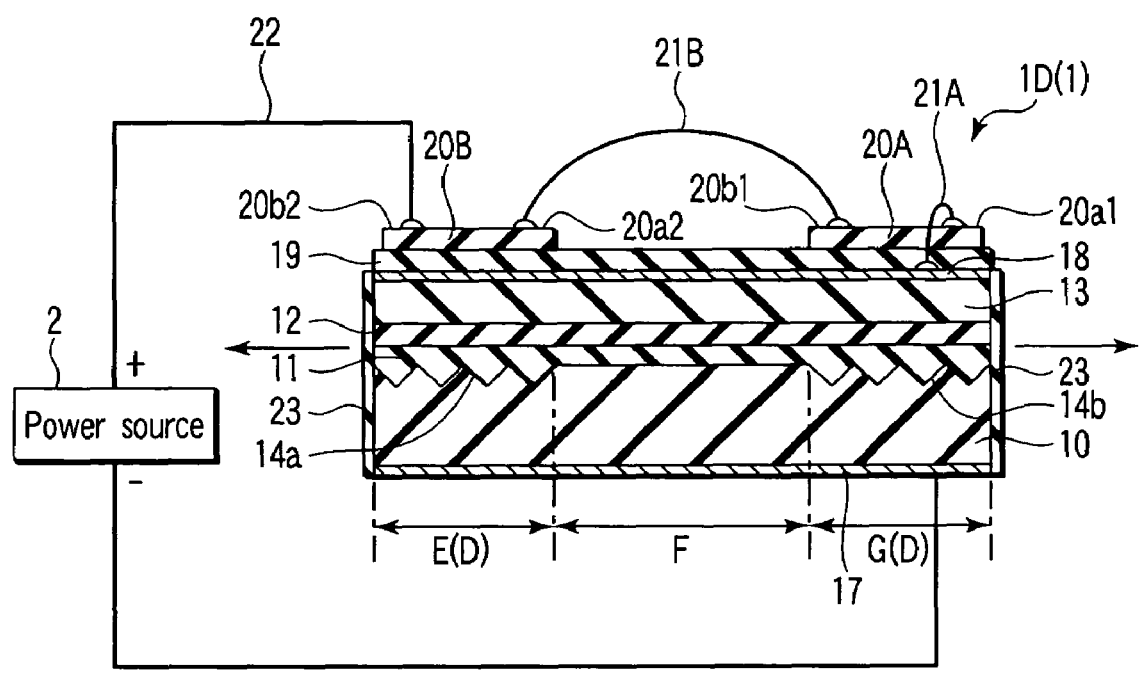
FIG. 5 is a schematic perspective view showing the configuration of a fourth embodiment of a tunable semiconductor laser device in accordance with the present invention.

FIG. 5 is a cross sectional view showing the configuration of the fourth embodiment of the tunable semiconductor laser device in accordance with the present invention.

With reference to FIG. 5, in the tunable semiconductor laser device, which is represented by numeral 1D(1), of the fourth embodiment, a first diffraction grating region E made of n-InGaAsP, a phase shift region F, and a second diffraction grating region G made of n-InGaAsP are formed above an n-InP substrate 10, which is a semiconductor substrate for making a multilayered semiconductor layer.

In this case, first and second diffraction gratings 14a and 14b are formed the first and second diffraction grating regions E and G, respectively.

Further, a light generating active layer 12 including a lower SCH layer, an MQW layer, and an upper SCH layer that are each made of InGaAsP having an appropriate composition are formed above the light guide layer 11.

A p-InP cladding layer 13 is formed above the active layer 12.

A pair of electrodes 17 and 18 are formed on the obverse and reverse surfaces of the semiconductor layer made as described above. More particularly, an n-type electrode 17 (first driving electrode) and p-type electrode 18 (second driving electrode) each made of a metal electrode are formed.

In the example shown in FIG. 5, the p-type electrode 18 is formed in a predetermined position above the p-InP cladding layer 13, and the n-type electrode 17 is formed on the lower surface of the n-InP substrate 10.

An antireflective film 23 is formed on each end facet (may be formed on one end facet) of the light guide layer 11 provided as a optical waveguide through which the laser beam is radiated.

First and second heating portions 20A and 20B formed of a thin-film resistor made of Pt, Au, or the like are, respectively, formed in portions opposite to the first and second diffraction grating regions E and G over the p-InP cladding layer. The respective heating portions are formed in such a manner as to cover the overall areas of the respective first and second diffraction gratings 14a and 14b via the insulation layer 19.

First heating terminals 20a1 and 20a2 and second heating terminals 20b1 and 20b2 are formed in the first and second heating portions 20A and 20B, respectively.

The first and second heating portions 20A and 20B are connected via wire to a single external power source 2 in series with the pair of electrodes 17 and 18.

In this case, the second driving electrode 18 (p-type electrode) and the first heating terminal 20a1 of the heating portion 20 are interconnected through a first connection line 21A formed of a bonding wire or the like. The second heating terminal 20b1 of the first heating portion 20A and the first heating terminal 20a2 of the second heating portion 20B are interconnected through a relaying connection line 21B formed of a bonding wire or the like.

The first driving electrode 17 (n-type electrode) and the second heating terminal 20b2 of the second heating portion 20B are interconnected via the external power source 2 through a second connection line 22 formed of a boding wire or the like.

In this manner, as shown in FIG. 2B, an equivalent circuit is configured such that the pair of electrodes 17 and 18 and the first and second heating portions 20A and 20B are connected in series to the single external power source 2 in the tunable semiconductor laser device 1.

Current of a single channel is supplied as driving power in synchronism from the single external power source 2 to both the interconnected portions between the first and second heating portions 20A and 20B and the pair of electrodes 17 and 18.

That is, as shown in FIG. 5, in the tunable semiconductor laser device 1 of the fourth embodiment, the wavelength control region D is formed of the first and second diffraction grating regions E and G formed in the light guide layer 11.

The first and second heating portions 20A and 20B are configured such that in the event of heating the first and second diffraction gratings 14a and 14b respectively formed in the first and second diffraction grating regions E and G included in the wavelength control region D, the first and second diffraction gratings 14a and 14b can be heated so that respective wavelengths selected in the respective diffraction gratings become equal to one another.

Thus, according to the fourth embodiment, the tunable semiconductor laser device 1 is realized in which the respective first and second diffraction gratings 14a and 14b formed in the first and second diffraction grating regions E and G included in the wavelength control region D are heated by the first and second heating portions 20A and 20B to largely vary the refractive indexes of the optical guide in the regions, whereby the wavelength of the light generated by the active layer 12 and the laser output can be controlled in a desired tunable wavelength range by using the single-channel current.

In addition, according to the fourth embodiment, the light wavelength generated by the active layer 12 and the laser output can be controlled by sharedly using the external single power source 2. Further, since the configuration is simplified, even in the case of adaptation to a portable gas detector in which no more than a single power source can be provided in a housing, the mounting space in the event of practical mounting can be as small as possible.

Description of Wavelength Characteristics

Wavelength characteristics of the tunable semiconductor laser device 1 according to the present invention and the conventional tunable semiconductor laser device will be described in more detail below with reference to FIGS. 6 and 7.

Figure 6:
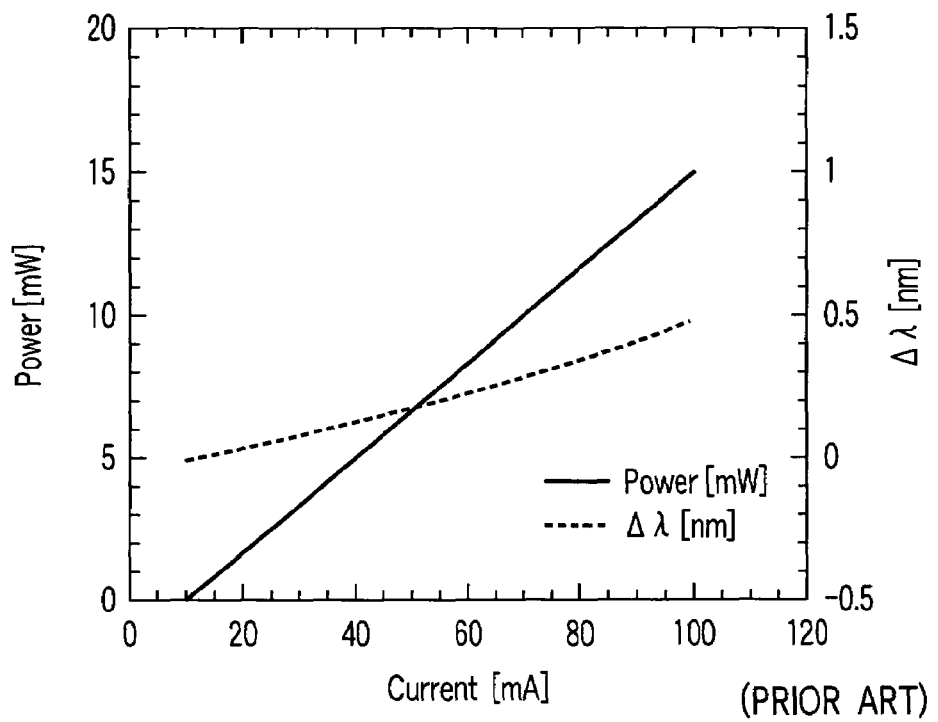
FIG. 6 is a diagram showing output characteristics of a conventional tunable semiconductor laser device.

FIG. 6 is a diagram showing output characteristics and wavelength characteristics of the conventional tunable semiconductor laser device.

FIG. 7 is a diagram showing output characteristics and wavelength characteristics of the tunable semiconductor laser device of the present invention.

In each of FIGS. 6 and 7, the characteristics shown by a solid line are output characteristics (Power mW) with respect to the driving current mA of the tunable semiconductor laser device, and the characteristics shown by a broken line are wavelength characteristics (wavelength shift amount $\Delta\lambda$ nm) with respect to the driving current mA of the tunable semiconductor laser device.

Figure 9:
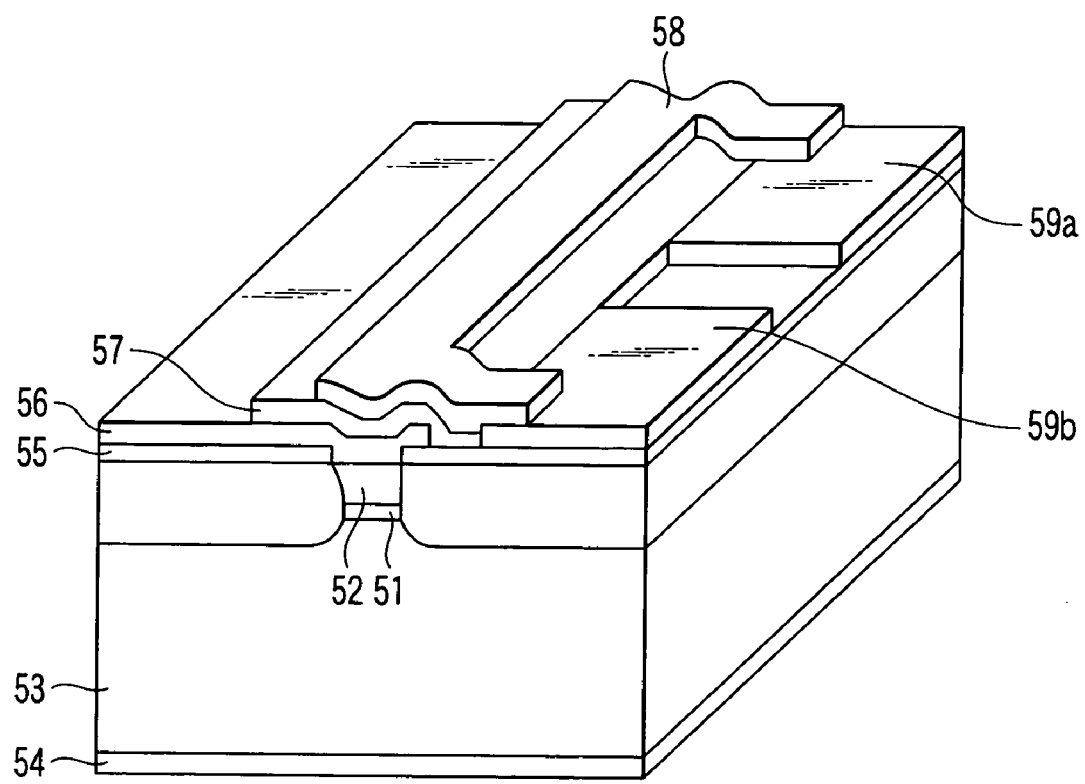
FIG. 9 is a schematic perspective view showing the configuration of a conventional DFB laser.
Figure 10A:
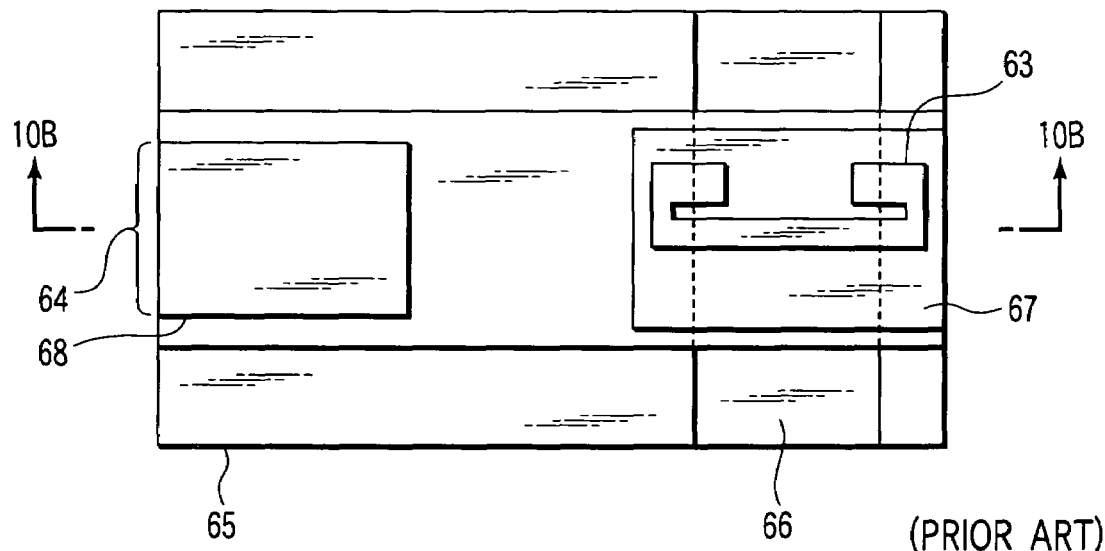
FIG. 10A is a schematic perspective view showing the configuration of a conventional DBR laser.
Figure 10B:
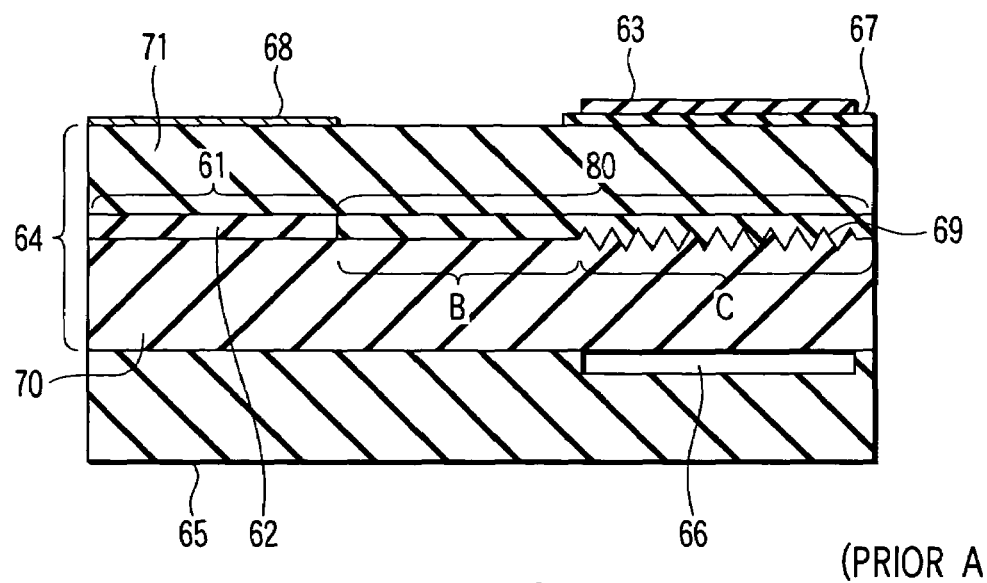
FIG. 10B is a cross sectional view taken along the line 10B-10B of FIG. 10A.

The wavelength characteristics of the tunable semiconductor laser device 1 of the present invention will be described referring as an example to the tunable semiconductor laser device 1B of the second embodiment of the present invention. Concurrently, the wavelength characteristics of the conventional tunable semiconductor laser device will be described referring as an example to the wavelength characteristics of a DFB laser without a heating portion shown in FIG. 9.

Ordinarily, tunable semiconductor laser devices of the type effecting single mode oscillation have characteristics in which light is radiated when the driving current supplied between a pair of electrodes exceeds a threshold current, and the wavelength of the radiation light increases proportionally to the square of the current value.

In the case of the conventional DFB laser without a heating portion, as shown in FIG. 6, it can be known that as the output is eventually raised by increasing the current value, the wavelength shift amount $\Delta\lambda$, shown by the broken line in FIG. 6, varies along a slow gradient as shown.

In comparison, in the case of the wavelength characteristics of the tunable semiconductor laser device 1B of the second embodiment of the present invention, the heating portion 20 heats the overall area of the diffraction grating 14 formed as the wavelength control region D in the overall area of the light guide layer 11. Accordingly, it can be known that, as shown in FIG. 7, as the output is raised by increasing the current value, then the gradient of the wavelength shift amount $\Delta\lambda$, shown by the broken line in FIG. 7, becomes sharp, and the variation amount in the wavelength shift amount $\Delta\lambda$ increases, compared to the conventional DFB laser without a heating portion.

More particularly, this indicates that, the refractive index variation of the optical waveguide of the tunable semiconductor laser device of the present invention is greater than the refractive index variation of the conventional DFB laser without a heating portion.

The respective examples shown in FIGS. 6 and 7 represent the wavelength characteristics of the conventional DFB laser without a heating portion and the tunable semiconductor laser device of the second embodiment of the present invention.

Accordingly, comparison results similar to the results described above were obtained even in the comparisons between the wavelength characteristics of the conventional DFB laser without a heating portion and the wavelength characteristics of the respective tunable semiconductor laser devices 1A, 1C, and 1D of the first, third, and fourth embodiments of the present invention.

In addition, in the cases of comparing the laser output values between the semiconductor laser device 1A of the first embodiment of the present invention and the respective tunable semiconductor laser devices 1B, 1C, and 1D of the second, third, and fourth embodiments of the present invention, the results are as follows. In the case of the tunable semiconductor laser devices 1B, 1C, and 1D in which the active layer 12 is directly heated by the heating portion 20 or first and second heating portions 20A and 20B, the laser output value is eventually saturated. However, in the case of the semiconductor laser device 1A, since the active region A (active layer 12) is not directly heated by the heating portion 20, the results were obtained in which the laser output value is not easily prone to saturation (not shown).

The above indicates that, compared with the tunable semiconductor laser devices 1B, 1C, and 1D of the second to fourth embodiments, the DBR laser formed of the tunable semiconductor laser device 1A of the first embodiment enables obtaining an even larger refractive index variation associated with the temperature.

Further, in the semiconductor laser device 1A of the first embodiment, since the regions other than the active region A (active layer 12) are heated by the heating portion 20, output reduction of the laser beam associated with the heated active region A (active layer 12) can be prevented. Thus, the configuration has the effect of enabling the lifetime of the tunable semiconductor laser device itself to be enhanced.

Fifth Embodiment

As a fifth embodiment of the present invention, a gas detector employing one of the tunable semiconductor laser devices 1 of the above-described first to fourth embodiments of the present invention will be described with respect to the overall configuration with reference to FIG. 8A.

Figure 8A:
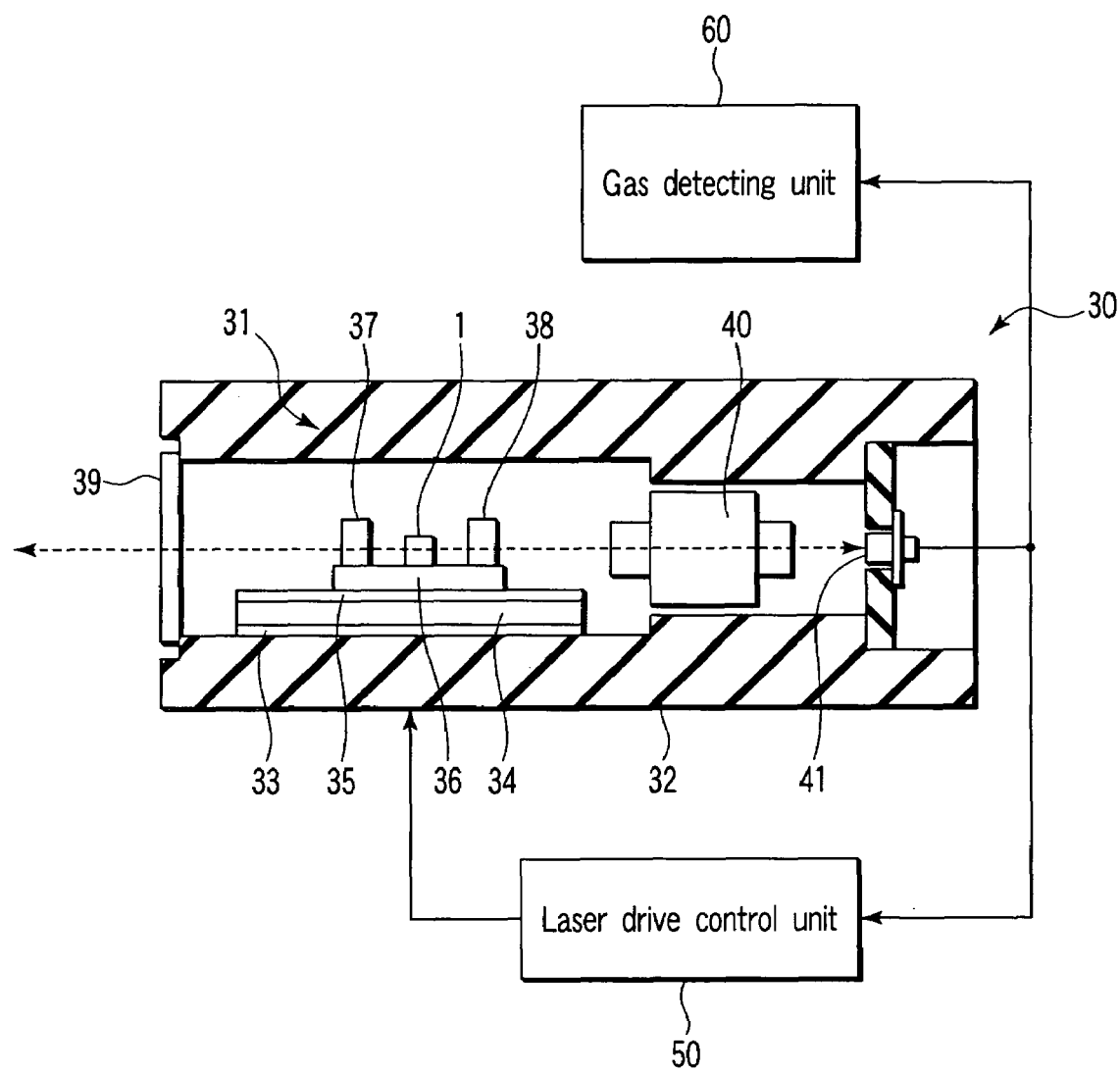
FIG. 8A is a schematic diagram of one example of a gas detector as a fifth embodiment employing the tunable semiconductor laser device of the present invention.

FIG. 8A is a schematic diagram of the configuration of one example of a gas detector as the fifth embodiment employing the tunable semiconductor laser device in accordance with the present invention.

As shown in FIG. 8A, in a gas detector 30 for performing the gas detection, a substrate 33 is provided inside a cylindrical casing 32 constituting a semiconductor laser module 31.

A temperature control device 35 formed of a Peltier device is mounted to a surface of a base 34 provided on the substrate 33.

In addition, the tunable semiconductor laser device 1, which is the one of the above-described first to fourth embodiments of the present invention, is mounted on a mounting base 36 provided on the temperature control device 35.

In this case, the tunable semiconductor laser device 1 is disposed to be capable of radiating the laser beam to the outside along the central axis of the cylindrical casing 32.

In the event of radiation of laser beam for measuring the concentration of a detection target gas towards a detection target, the tunable semiconductor laser device 1 undergoes temperature control by the temperature control device 35, which is formed from the Peltier device, through a temperature stabilization PID circuit 55 of a laser drive control unit 50 shown in FIG. 8B, which is described in detail below, whereby the laser beam is controlled to a wavelength matched for the detection target gas.

In the case of the gas detector 30 having the configuration shown in FIG. 8A, the laser beam from the tunable semiconductor laser device 1 is radiated to both sides of the detection target gas and a reference gas.

Converging lenses 37 and 38 for converging respective rays of laser beam radiated to the side of the detection target gas and the side of the reference gas to be a parallel beam are provided to be positioned along the lens optical axis on both sides of the tunable semiconductor laser device 1 on the mounting base 36.

Thereby, the laser beam from the tunable semiconductor laser device 1 to the side of the detection target gas is output to the outside through the converging lens 37 and a protection glass 39 provided to protect the semiconductor laser module 31, and is then radiated into the detection space.

The laser beam to the side of the reference gas from the tunable semiconductor laser device 1 is formed by the converging lens 38 to the parallel beam, and is detected by a photodetector 41 through a reference gas cell 40.

The reference gas cell 40 is a cell filled with the detection target gas for use as the reference gas, and is used as follows. In accordance with a detection output of the laser beam radiated to the side of the reference gas and detected by the photodetector 41 through the reference gas cell 40, the wavelength of the laser beam radiated from the tunable semiconductor laser device 1 is tuned to the absorption line of the detection target gas by using a wavelength stabilization control circuit 54 of the laser drive control unit 50 shown in FIG. 8B, which is described in detail below.

The photodetector 41 detects reflected and returned laser beam of the laser beam radiated into the detection space, then converts the received laser beam to an electric signal (current), and supplies the electric signal (current) to a gas detecting unit 60 shown in FIG. 8C, which is described in detail below.

As described further below, the gas detecting unit 60 detects a fundamental harmonic level and a double harmonic level from the electric signal converted by the photodetector 41, performs the division of the double harmonic level by the fundamental harmonic level, and then performs measurements to detect the presence or absence, the concentration, and the like of the detection target gas in accordance with a value obtained by the division.

Figure 8B:
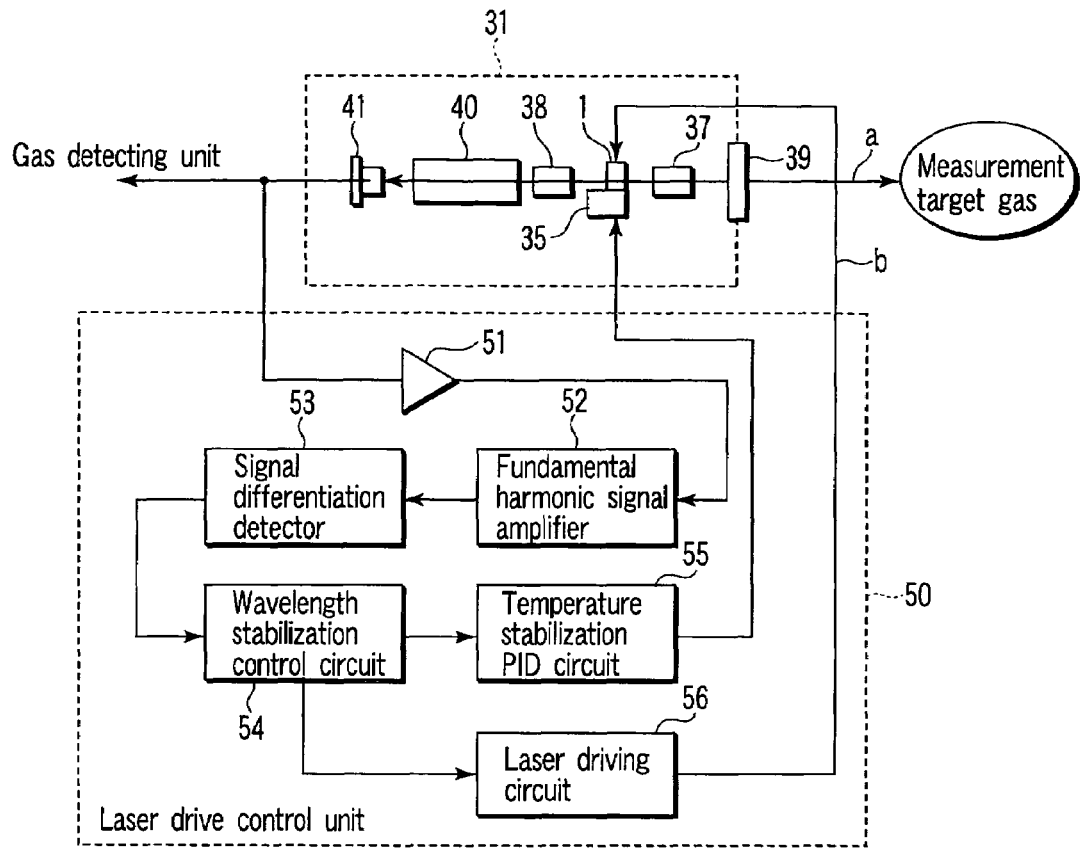
FIG. 8B is a diagram showing the overall configurations of a semiconductor laser module 31 and a laser drive control unit 50 which are shown in FIG. 8A.
Figure 8C:
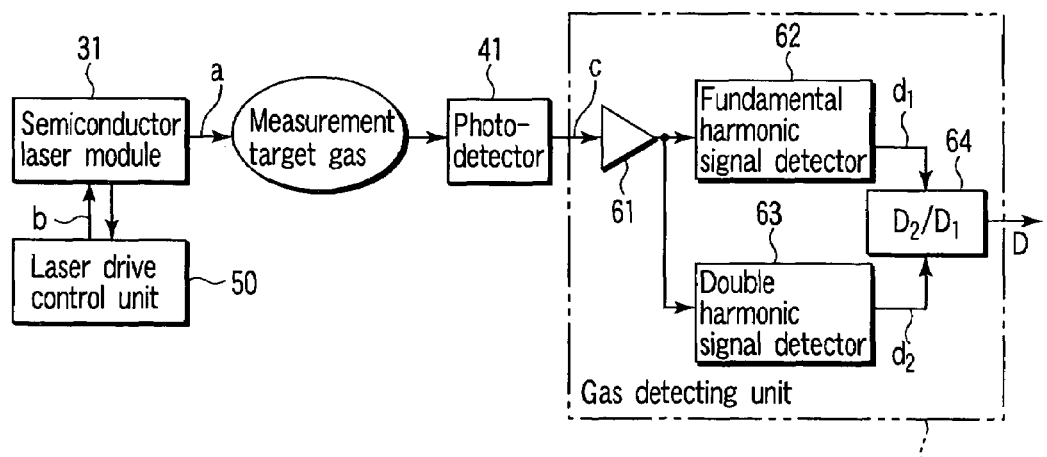
FIG. 8C is a diagram showing the overall configurations of the gas detector and a gas detecting unit 60 which are shown in FIG. 8A.

FIGS. 8A to 8C and descriptions relevant thereto have omitted illustration and description of the configuration of the tunable semiconductor laser device 1 of one of the first to fourth embodiments of the present invention, in which, as described above, the pair of electrodes 17 and 18 and the heating portion 20 (or, 20A and 20B) are connected in series to the single external power source 2, whereby the driving current is supplied synchronously to the pair of electrodes 17 and 18 and the heating portion 20 (or, 20A and 20B) from the single external power source 2.

FIG. 8B is a diagram showing the overall configurations of the semiconductor laser module 31 and the laser drive control unit 50.

The laser drive control unit 50 is configured to include a current-voltage converter 51, a fundamental harmonic signal amplifier 52, a signal differentiation detector 53, the wavelength stabilization control circuit 54, the temperature stabilization PID circuit 55, and a laser driving circuit 56.

The current-voltage converter 51 converts the electric signal, which has been received from the photodetector 41, to the voltage. The fundamental harmonic signal amplifier 52 amplifies the voltage converted by the current-voltage converter 51. The signal differentiation detector 53 performs differentiation of a voltage waveform amplified by the fundamental harmonic signal amplifier 52 and generates an offset signal that is offset from an absorption central wavelength $\lambda_0$ of the reference gas.

The wavelength stabilization control circuit 54 stabilizes an emission wavelength $\lambda$ of the tunable semiconductor laser device 1 to the absorption central wavelength $\lambda_0$ of the reference gas.

More particularly, the wavelength stabilization control circuit 54 converts the offset signal, which has been received from the signal differentiation detector 53, to the temperature of the tunable semiconductor laser device 1, outputs the result to the temperature stabilization PID circuit 55, and outputs a control signal to the reference gas cell 40 in accordance with an offset signal representing an offset therefrom.

The temperature stabilization PID circuit 55 controls the temperature control device 35 formed of the Peltier device. More particularly, in accordance with a temperature signal from the wavelength stabilization control circuit 54, the temperature stabilization PID circuit 55 provides PID control so that the tunable semiconductor laser device 1 is set to a temperature causing oscillation at a desired wavelength, thereby stably maintaining the temperature of the tunable semiconductor laser device 1 at a desired temperature.

With respect to the center corresponding to a central current value (bias current value) or a value at which the oscillation wavelength of the tunable semiconductor laser device 1 corresponds to the absorption central wavelength of the absorption characteristic of the reference gas (gas to be measured), the laser driving circuit 56 applies a modulation signal b having predetermined amplitude and modulation frequency to the tunable semiconductor laser device 1 incorporated into the semiconductor laser module 31.

As a consequence, laser beam whose wavelength is variable depending on a predetermined amplitude and frequency with respect to the absorption central wavelength is output from the semiconductor laser module 31.

In accordance with the temperature signal from the wavelength stabilization control circuit 54, the laser driving circuit 56 controls the central current value (bias current value) to enable obtaining the above-described wavelength characteristic of the laser beam a having been output from the semiconductor laser module 31.

Thus, in the gas detector of the fifth embodiment, the laser beam radiated from the tunable semiconductor laser device 1 is caused to transmit through the reference gas cell 40 filled with the gas identical to the measurement target gas, in which the temperature of the tunable semiconductor laser device 1 and the central current value (bias current value) of the modulation signal b applied to the tunable semiconductor laser device 1 are automatically controlled so that the central wavelength of the laser beam matches with the absorption central wavelength of the absorption characteristics of the reference gas (measurement target gas).

FIG. 8C is a diagram showing the overall configurations of the gas detector and the gas detecting unit 60 which are shown in FIG. 8A.

With reference to FIG. 8C, the laser beam a wavelength-modulated with respect to the absorption central wavelength output from the semiconductor laser module 31 is absorbed corresponding to the absorption characteristics in the stage of transmission of the measurement target gas; and thereafter, the laser beam received by the photodetector 41 is converted to an electric (current) signal c, and is input to the gas detecting unit 60.

For the convenience of description, FIG. 8C shows the photodetector 41 independently of the semiconductor laser module 31.

The detailed configuration of the laser drive control unit 50 and the operation thereof are already described above with reference to FIG. 8B.

The gas detecting unit 60 includes a current-voltage converter 61, a fundamental harmonic signal detector 62, a double harmonic signal detector 63, and a divider 64.

The current-voltage converter 61 converts an electric (current) signal c of an input current to an electric signal c of voltage, and sends the converted signal to the fundamental harmonic signal detector 62 and the double harmonic signal detector 63.

The fundamental harmonic signal detector 62 extracts a fundamental harmonic signal $d_1$, which is a signal component of the modulation frequency contained in the input electric signal c, and sends the extracted signal to the divider 64.

The double harmonic signal detector 63 extracts a double harmonic signal $d_2$, which is a signal component of a double frequency of the modulation frequency contained in the input electric signal c, and sends the extracted signal to the divider 64.

The divider 64 calculates a ratio $(D_2/D_1)$ between an amplitude $D_2$ of the double harmonic signal $d_2$ and an amplitude $D_1$ of the fundamental harmonic signal $d_1$, and outputs the calculated ratio $(D_2/D_1)$ as a detection value D $(=D_2/D_1)$ corresponding to a corresponding gas concentration.

As described above, the tunable semiconductor laser device 1 of the present invention is configured such that the pair of electrodes 17 and 18 and the heating portion 20 (or, 20A and 20B) are connected in series to the single external power source 2, whereby the driving current is supplied synchronously to the pair of electrodes 17 and 18 and the heating portion 20 (or, 20A and 20B) from the single external power source 2.

Accordingly, in the event of gas detection by the TDLAS scheme by employing the tunable semiconductor laser device 1 of the present invention, the refractive index variation can be increased to thereby control the wavelength in a desired tunable wavelength range and the laser output by using the single-channel current.

In addition, in the event of control of the laser output and the wavelength, since the single power source is sharedly used, only the single power source need be provided to accomplish the operation.

Consequently, the configuration of the tunable semiconductor laser device 1 of the present invention is simplified, such that the tunable semiconductor laser device 1 can be used by being incorporated in the portable gas detector 30 in which the power consumption is low, and the component-mounting space in the case, the power source capacity, and the like are restricted.

Further, when the tunable semiconductor laser device of the first embodiment is employed, the configuration is formed in which the active area A (active layer 12) is not directly heated by the heating portion 20, such that the lifetime of the device itself can be enhanced.

In the respective tunable semiconductor laser device 1C or 1D of the third or fourth embodiment, the diffraction grating 14 is provided at one end or each of both ends in the region sandwiched by the antireflective films 21.

However, the present invention is not limited to such a configuration, but the configuration of the present invention (configuration in which a pair of electrodes and the heating portion are connected in series to the single power source) can also be employed in a tunable semiconductor laser device having at least a single diffraction grating region in the optical waveguide.

More particularly, the configuration of the tunable semiconductor laser device 1 of the present invention can be such that the heating portion 20 (20A, 20B) is disposed, preferably, in a region free of mode hopping, and the pair of electrodes 17 and 18 and the heating portion 20 (20A, 20B) are connected in series to the single external power source.

While the most preferred embodiments of the present invention have been described above, the present invention is not limited by the descriptions and drawings regarding the most preferred embodiments.

Of course, other embodiments, examples, operational techniques that could be implemented by those skilled in the art in accordance with the most preferred embodiments are all included in the scope of the present invention.

The invention claimed is:

1. A tunable semiconductor laser device, comprising:
   a semiconductor substrate;
   an active layer that is formed above the semiconductor substrate and that generates light;
   a wavelength control region that (i) is formed to include the active layer, is (ii) formed in an optical waveguide which guides the light generated by the active layer, and (iii) includes in at least one portion a diffraction grating which selects light having a predetermined wavelength from the light generated by the active layer;
   a cladding layer formed above the optical waveguide;
   an insulation film formed above the cladding layer;
   a first driving electrode formed below the semiconductor substrate;
   a second driving electrode formed above the cladding layer;
   a heating portion that is formed above the insulation film and that is used to heat at least one portion of the wavelength control region;
   a first heating terminal and a second heating terminal that are provided in the heating portion;
   a first connection line that connects between the second driving electrode and the first heating terminal; and
   a second connection line that connects between the first driving electrode and the second heating terminal through a power source,
   wherein current supplied from the power source to the first and second connection lines connected in series through the heating portion is tuned, whereby the wavelength of light emitted to an outside from the optical waveguide can be controlled.

2. The tunable semiconductor laser device according to claim 1, wherein:
   the wavelength control region includes a distributed Bragg reflector region in which the diffraction grating is provided and a phase adjust region adjacent to the distributed Bragg reflector region; and
   the heating portion is configured to be capable of heating at least one portion of the phase adjust region.

3. The tunable semiconductor laser device according to claim 2, wherein the heating portion is configured further to be capable of uniformly heating an overall area of the distributed Bragg reflector region.

4. The tunable semiconductor laser device according to claim 1, wherein:
   the wavelength control region has one diffraction grating; and
   the heating portion is configured to be capable of uniformly heating an overall area of the one diffraction grating.

5. The tunable semiconductor laser device according to claim 4, wherein the one diffraction grating is formed across an overall area of the optical waveguide.

6. The tunable semiconductor laser device according to claim 4, wherein the one diffraction grating is formed in one portion of the optical waveguide.

7. The tunable semiconductor laser device according to claim 1, wherein:

the wavelength control region has a plurality of diffraction gratings formed in a plurality of portions of the optical waveguide; and the heating portion is configured to be capable of heating the plurality of diffraction gratings so that respective wavelengths selected by respective ones of the plurality of diffraction gratings are identical to one another.

8. The tunable semiconductor laser device according to claim 7, wherein the heating portion is formed of a plurality of heating portions that discretely heat the plurality of diffraction gratings, and the plurality of heating portions are connected in series.

9. The tunable semiconductor laser device according to claim 1, wherein the heating portion is formed of a thin-film resistor.

10. The tunable semiconductor laser device according to claim 1, wherein the tunable semiconductor laser device is employed in a gas detector that radiates a laser beam having a predetermined wavelength into a detection space, and that performs gas detection by using a tunable diode laser absorption spectroscopy scheme utilizing a characteristic that the laser beam is absorbed by a detection target gas.

11. A gas detector that includes a tunable semiconductor laser device, that radiates a laser beam having a predetermined wavelength into a detection space, and that performs gas detection by using a tunable diode laser absorption spectroscopy scheme utilizing a characteristic that the laser beam is absorbed by a detection target gas, wherein the tunable semiconductor laser device comprises:
a semiconductor substrate;
an active layer that is formed above the semiconductor substrate and that generates light;
a wavelength control region that (i) is formed to include the active layer, (ii) is formed in an optical waveguide which guides the light generated by the active layer, and (iii) includes in at least one portion a diffraction grating which selects light having a predetermined wavelength from the light generated by the active layer;
a cladding layer formed above the optical waveguide;
an insulation film formed above the cladding layer;
a first driving electrode formed below the semiconductor substrate;
a second driving electrode formed above the cladding layer;
a heating portion that is formed above the insulation film and that is used to heat at least one portion of the wavelength control region;
a first heating terminal and a second heating terminal that are provided in the heating portion;
a first connection line that connects between the second driving electrode and the first heating terminal; and
a second connection line that connects between the first driving electrode and the second heating terminal through a power source,
wherein current supplied from the power source to the first and second connection lines connected in series through the heating portion is tuned, whereby the wavelength of light emitted to an outside from the optical waveguide can be controlled.

12. The gas detector according to claim 11, wherein:
the wavelength control region includes a distributed Bragg reflector region in which the diffraction grating is provided and a phase adjust region adjacent to the distributed Bragg reflector region; and
the heating portion is configured to be capable of heating at least one portion of the phase adjust region.

13. The gas detector according to claim 12, wherein the heating portion is configured further to be capable of uniformly heating an overall area of the distributed Bragg reflector region.

14. The gas detector according to claim 11, wherein:
the wavelength control region has one diffraction grating; and
the heating portion is configured to be capable of uniformly heating an overall area of the one diffraction grating.

15. The gas detector according to claim 14, wherein the one diffraction grating is formed across an overall area of the optical waveguide.

16. The gas detector according to claim 14, wherein the one diffraction grating is formed in one portion of the optical waveguide.

17. The gas detector according to claim 11, wherein:
the wavelength control region has a plurality of diffraction gratings formed in a plurality of portions of the optical waveguide; and
the heating portion is configured to be capable of heating the plurality of diffraction gratings so that respective wavelengths selected by respective ones of the plurality of diffraction gratings are identical to one another.

18. The gas detector according to claim 17, wherein the heating portion is formed of a plurality of heating portions that discretely heat the plurality of diffraction gratings, and the plurality of heating portions are connected in series.

19. The gas detector according to claim 11, wherein the heating portion is formed of a thin-film resistor.

20. A method for manufacturing a tunable semiconductor laser device, the method comprising:
forming an optical waveguide above a semiconductor substrate, the optical waveguide including an active layer that generates light, and a wavelength control region including in at least one portion a diffraction grating which selects and reflects light having a predetermined wavelength from the light generated by the active layer;
forming a cladding layer above the optical waveguide;
forming an insulation film above the cladding layer;
forming a first driving electrode below the semiconductor substrate;
forming a second driving electrode above the cladding layer;
forming a heating portion above the insulation film, for being used to heat at least one portion of the wavelength control region;
forming a first heating terminal and a second heating terminal in the heating portion;
connecting between the second driving electrode and the first heating terminal by using a first connection line; and
connecting between the first driving electrode and the second heating terminal through a power source by using a second connection line,
wherein in the manufactured tunable semiconductor laser device, current supplied from the power source to the first and second connection lines connected in series through the heating portion is tuned, whereby the wavelength of the light emitted to an outside from the optical waveguide can be controlled.

21. The method for manufacturing a tunable semiconductor laser device according to claim 20, wherein:
the wavelength control region includes a distributed Bragg reflector region in which the diffraction grating is provided and a phase adjust region adjacent to the distributed Bragg reflector region; and
the heating portion is configured to be capable of heating at least one portion of the phase adjust region.

22. The method for manufacturing a tunable semiconductor laser device according to claim 21, wherein the heating portion is configured further to be capable of uniformly heating an overall area of the distributed Bragg reflector region.

23. The method for manufacturing a tunable semiconductor laser device according to claim 20, wherein:

the wavelength control region has one diffraction grating; and the heating portion is configured to be capable of uniformly heating an overall area of the one diffraction grating.

24. The method for manufacturing a tunable semiconductor laser device according to claim 23, wherein the one diffraction grating is formed across an overall area of the optical waveguide.

25. The method for manufacturing a tunable semiconductor laser device according to claim 23, wherein the one diffraction grating is formed in one portion of the optical waveguide.

26. The method for manufacturing a tunable semiconductor laser device according to claim 20, wherein:

the wavelength control region has a plurality of diffraction gratings formed in a plurality of portions of the optical waveguide; and the heating portion is configured to be capable of heating the plurality of diffraction gratings so that respective wavelengths selected by respective ones of the plurality of diffraction gratings are identical to one another.

27. The method for manufacturing a tunable semiconductor laser device according to claim 26, wherein the heating portion is formed of a plurality of heating portions that discretely heat the plurality of diffraction gratings, and the plurality of heating portions are connected in series.

28. The method for manufacturing a tunable semiconductor laser device according to claim 20, wherein the heating portion is formed of a thin-film resistor.

* * * * *